United States Patent [19]
Pallos et al.

[11] 3,968,252
[45] July 6, 1976

[54] DERIVATIVES OF CERTAIN GERANYL PHENYL ETHERS AND THEIR USE IN CONTROLLING INSECTS

[75] Inventors: Ferenc M. Pallos, Walnut Creek; Chien K. Tseng, El Cerriot, both of Calif.

[73] Assignee: Stauffer Chemical Company, Westport, Conn.

[22] Filed: Mar. 6, 1975

[21] Appl. No.: 555,764

Related U.S. Application Data

[62] Division of Ser. No. 376,772, July 5, 1973, Pat. No. 3,888,987, which is a division of Ser. No. 198,018, Nov. 4, 1971, Pat. No. 3,772,365.

[52] U.S. Cl. .............................. 424/337; 424/278; 424/304; 424/340; 424/341; 424/DIG. 12; 260/609 R
[51] Int. Cl.² ..................... A01N 9/12; A01N 9/14
[58] Field of Search ................ 260/613 R; 424/340, 424/337

[56] References Cited
UNITED STATES PATENTS
3,711,519    1/1973    Dolejs et al. .................... 260/348 R Primary Examiner—V. D. Turner
Attorney, Agent, or Firm—Edwin H. Baker

[57] ABSTRACT

Compounds having the formula

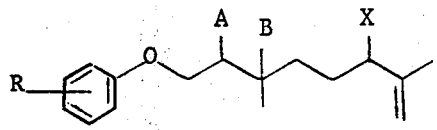

in which R is hydrogen, lower alkyl, lower alkenyl, lower alkoxy, halogen, nitro; or lower alkylthio; X is chlorine or bromine; A and B are each hydrogen, together form an epoxide link or together form a bond; the use of these compounds in controlling insects; and a method of preparing these compounds.

7 Claims, No Drawings

DERIVATIVES OF CERTAIN GERANYL PHENYL ETHERS AND THEIR USE IN CONTROLLING INSECTS

This is a division of application Ser. No. 376,772 filed July 5, 1973 now U.S. Pat. No. 3,888,987 which is a division of application Ser. No. 198,018 filed Nov. 4, 1971, now U.S. Pat. No. 3,772,365.

This invention relates to the use of certain novel chemical compounds in controlling insects, more particularly, the chemical compounds are certain derivatives of phenyl geranyl ethers. The invention also relates to a method of preparing the compounds.

It has been found that there is a class of compounds which acts in a different manner on insects than presently used insecticides and exerts a disrupting influence upon the normal development of insects. Such compounds impede the metamorphosis of the normal pupation of pest insects and result in the formation of numbers of the treated species which are not viable or sterile. This ultimately leads, indirectly at least, to the destruction of a pest population.

The compounds of the present invention are believed to have the further advantages that they are non-toxic to warm-blooded animals and highly effective to control insects at low dosages. It is also hoped that it will be more difficult for insects to develop resistance againt these compounds.

One embodiment of the present invention is concerned with novel pesticidal compositions.

In another embodiment, the invention is concerned with the active pesticidal component of such compositions.

In still another embodiment, the invention is concerned with a process for controlling insects by hindering or impeding the metamorphosis and reproduction of the insects.

And in another embodiment, the invention is concerned with a process for preparing certain epoxidized compounds.

The compounds of the present invention that are useful in controlling insects are those having the formula

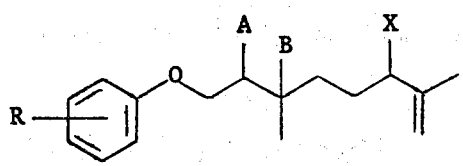

in which R is hydrogen; halogen; lower alkyl having 1 to 6 carbon atoms, preferably 1 to 4 carbon atoms; lower alkoxy having 1 to 4 carbon atoms, preferably 1 to 2 carbon atoms; lower alkenyl, having 2 to 6 carbon atoms, preferably 3 to 4 carbon atoms; lower alkylthio having 1 to 4 carbon atoms, preferably 1 to 2 carbon atoms, or nitro, most preferably, R is in the para-position; X is chlorine or bromine; and A and B are each hydrogen, together form an epoxide link or together form a bond. The term halogen covers chlorine, bromine, iodine and fluorine.

Carbon atoms, joined to two or less hydrogen atoms, occupy each angle in the backbone of the compound represented by the above formula unless otherwise specified. Letters at the terminals and branches have been used to show the attached groups.

The certain halogenating agents recited herein are t-alkyl hypochlorite, preferably t-butyl hypochlorite; t-alkyl hypobromite, preferably t-butyl hypobromite; HOCl, HOBr; or N-bromolimides, preferably N-bromosuccinimide.

As indicated heretofore, the above compounds are useful in impeding the metamorphosis and/or the reproduction of insects. The activity of the compounds is such that insects at any stage of their development can be effectively treated therewith.

Reaction No. 1

The compound having the formula

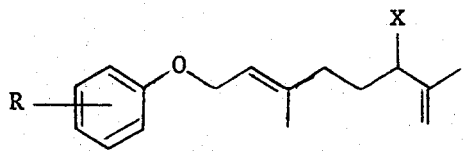

in which R and X are defined can be prepared by the following reaction:

1) 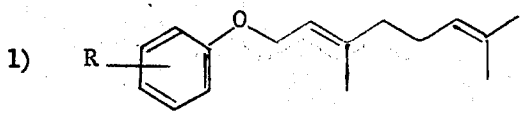

+ Certain Halogenating Agent in which R is as defined.

Preferably, reaction number 1 is carried out in a solvent such as methylene chloride, preferably the certain halogenating agent is added slowly with stirring and at a temperature sufficient to give a controlled reaction, such as about 0°C. to about 10°C. Preferably reaction number 1 is carried out using about equal mole amounts of the reactants, or with a slight excess of the halogenating agent. The reaction product is recovered by conventional means.

Reaction No. 2

The compounds having the formula

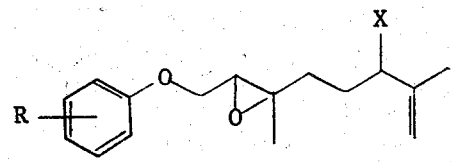

in which R and X are as defined, can be prepared by the following reaction:

2) 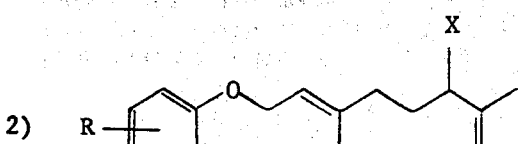

+ epoxidizing agent in which R and X are as defined.

Preferably, reaction number 2 is carried out in a solvent such as methylene chloride, preferably the epoxidizing agent is added slowly with stirring at a temperature sufficient to give a controlled reaction, such as about 5°C. to about 10°C. Preferably reaction number 2 is carried out using about equal mole amounts of the reactants, or with a slight excess of the epoxidizing agent. The reaction product is recovered by conventional means.

The epoxidizing agents are well-known to those skilled in the art and include such materials as meta-chloroperbenzoic acid. References are made to *Kirk-Othmer Encyclopedia of Chemical Technology*, 2nd Edition, 1965, Vol. 8, pages 238–244, for a discussion of various types of epoxidizing agents.

Reaction No. 3

Compounds having the formula

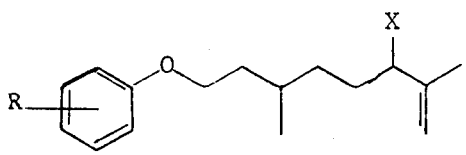

in which R and X are as defined, can be prepared by the following reactions:

3) 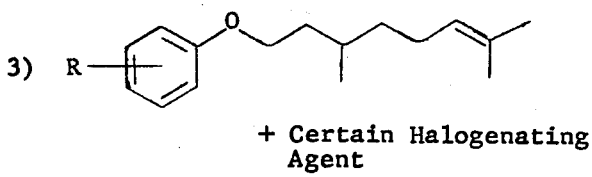

+ Certain Halogenating Agent in which R is as defined.

Preferably, reaction number 3 is carried out in a solvent such as methylene, chloride, preferably the certain halogenating agent is added slowly with stirring and at a temperature sufficient to give a controlled reaction, such as about 0°C. to about 10°C. Preferably reaction number 3 is carried out using about equal mole amounts of the reactants, or with a slight excess of the halogenating agent. The reaction product is recovered by conventional means.

A process of this invention is one for preparing a compound of the formula:

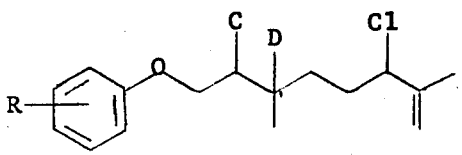

in which R is hydrogen; halogen, lower alkyl having 1 to 6, carbon atoms; lower alkoxy having 1 to 4 carbon atoms; lower alkenyl having 2 to 6 carbon atoms; lower alkylthio having 1 to 4 carbon atoms; or nitro; and C and D are each hydrogen, or together form a bond comprising the step of reacting a compound of the formula:

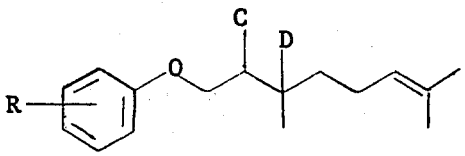

in which R, C and D are as defined with t-butyl hypochlorite, or HOCl.

Preferably, the reaction is carried out in a solvent such as methylene chloride, preferably the recited chlorinating agent is added slowly with stirring and at a temperature sufficient to give a controlled reaction, such as about 0°C. to about 10°C. Preferably the reaction is carried out using about equal mole amounts of the reactants, or with a slight excess of the chlorinating agent. The reaction product is recovered by conventional means.

Another process of this invention is one for preparing a compound of the formula:

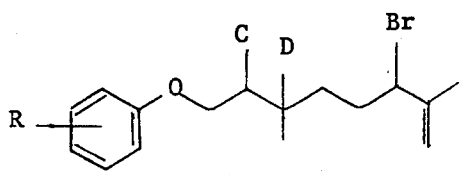

in which R is hydrogen; halogen; lower alkyl having 1 to 6 carbon atoms; lower alkoxy having 1 to 4 carbon atoms; lower alkenyl having 2 to 6 carbon atoms; lower alkylthio having 1 to 4 carbon atoms; or nitro; and C and D are each hydrogen, or together form a bond comprising the step of reacting a compound of the formula:

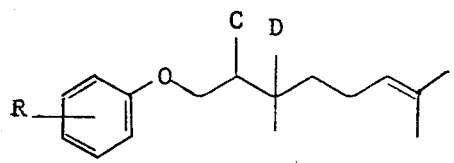

in which R, C and D are as defined with t-butyl hypobromite HOBr or N-bromosuccinimide.

Preferably the reaction is carried out in a solvent such as methylene chlorine, preferably the brominating agent is added slowly with stirring and at a temperature sufficient to give a reaction is carried out using about equal mole amounts of the reactants, or with a slight excess of the brominating agent. The reaction product is recovered by conventional means.

Preparation of the compounds of this invention is illustrated by the following specific examples.

EXAMPLE I 1-(4'-ethyl) phenoxy-3,7-dimethyl-6-chloro-2,7-octadiene

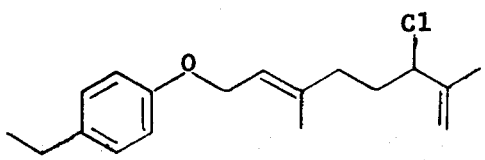

2.58 g. (0.01 mole) of a compound of the formula

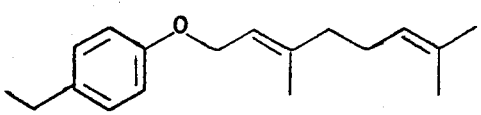

is dissolved in 25 ml. CH$_2$Cl$_2$ and cooled in an ice bath. Slowly 1.1 g. (0.01 mole) t-butylhypochlorite in 10 ml. CH$_2$Cl$_2$ is added dropwise at a temperature of 0–5°C. The mixture is stirred in an ice bath for ½ hour and at room temperature for 1 hour and allowed to stand overnight. The reaction product is worked up by adding 15 ml. CH$_2$Cl$_2$ and the mixture is washed with water, with 10% NaHCO$_3$ twice, dried over MgSO$_4$ filtered and stripped to yield 2.3 g. of the desired product, $N_D^{30}$ 1.5200. The structure is confirmed by I.R., n.m.r. and mass spectroscopy.

EXAMPLE II 1-(4'-ethyl) phenoxy-3,7-dimethyl-6-chloro-2,7-octadiene

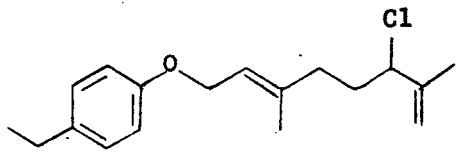

12.5 ml. of a 5.5% solution of NaOCl are stirred and cooled in an ice bath. A mixture of 2.58 gr. (0.01 mole) of a compound of the formula

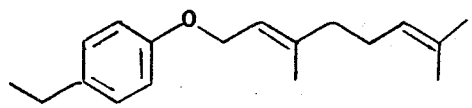

and 0.7 gr. CH₃COOH acetic acid glacial are added at once. The acetic acid and the NaOCl react to form HCCl in situ. Temperature goes from 8° to 26°C. The mixture is stirred for ½ hour. The reaction product is recovered by adding CH₂Cl₂, separating the organic layer. This is washed with 10% NaHCO₃ solution, dried over MgSO₄, filtered and stripped to yield 2.1 gr. of the desired product $N_D^{30}$ 1.5220. The structure is confirmed by I.R. and n.m.r. spectroscopy.

EXAMPLE III 1-(4'-ethyl) phenoxy-3,7-dimethyl-6-bromo-2,7-octadiene

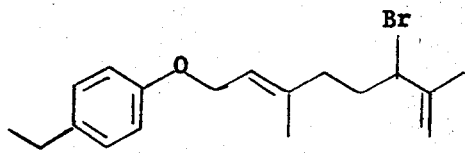

1.3 gr. (0.005 mole) of a compound of the formula

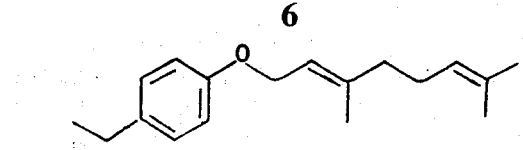

is dissolved in 15 ml. 1,2-dimethoxyethane and 1.8 gr. (0.015 mole) N-bromosuccinimide are mixed at a temperature of 0° to 5°C. and stirred at room temperature overnight. The mixture is evaporated to dryness with a water aspirator. 50 ml. CCl₄ is added and the mixture stirred. A solid form is removed by filtration. The solid is washed with CCl₄. The organic layers are combined, washed twice with water, dried over MgSO₄, filtered and stripped. 1.9 gr. of the desired product is obtained, $N_D^{30}$ 1.4570. I.R. and n.m.r. spectroscopy confirm the structure.

EXAMPLE IV 3,7-dimethyl-6-chloro-1-p-ethylphenoxy-2,3-epoxy-7-octene

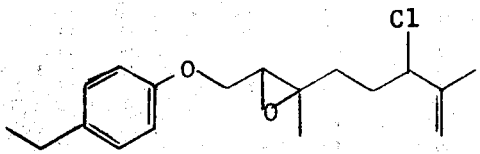

1.17 gr. (0.004 mole) of the reaction product of Example 1 is dissolved in 10 ml. CH₂Cl₂, 0.004 mole of m-chloroperbenzoic acid solution in CH₂Cl₂ are slowly added dropwise at 0° to 5°C. temperature. The mixture is stirred at room temperature overnight, then washed with 10 ml. NaHCO₃ three times, dried over MgSO₄, filtered and stripped to yield 0.9 grams of the desired product $N_D^{30}$ 1.5160. The structure is confirmed by I.R. n.m.r. mass spectroscopy.

The following is a table of certain selected compounds that are preparable according to the procedures described hereto. Compound numbers are assigned to each compound and are used throughout the remainder of the specification.

TABLE I

| COMPOUND NUMBER | R¹ | R² | X | A & B | R |
|---|---|---|---|---|---|
| 1 | CH₃ | CH₃ | Cl | bond | 4-CH₃—S— |
| 2 | CH₃ | CH₃ | Cl | bond | 4-C₂H₅ |
| 3 | CH₃ | CH₃ | Br | bond | 4-C₂H₅ |
| 4 | CH₃ | CH₃ | Cl | bond | H |
| 5 | CH₃ | CH₃ | Cl | bond | 4-CH₃ |
| 6 | CH₃ | CH₃ | Br | bond | 4-i-C₃H₇ |
| 7 | CH₃ | CH₃ | Cl | bond | 4-NO₂ |
| 8 | CH₃ | CH₃ | Cl | bond | 3-Cl |
| 9 | CH₃ | CH₃ | Br | bond | 4-Cl |
| 10 | CH₃ | CH₃ | Cl | bond | 4-Br |
| 11 | CH₃ | CH₃ | Cl | bond | 4-I |
| 12 | CH₃ | CH₃ | Br | bond | 4-F |
| 13 | CH₃ | CH₃ | Cl | bond | 4-CN |

TABLE I-continued

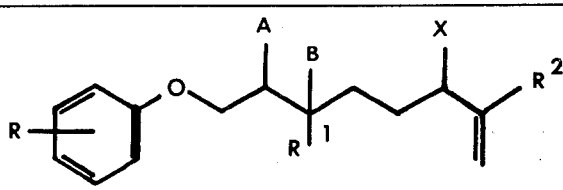

| COMPOUND NUMBER | R¹ | R² | X | A & B | R |
|---|---|---|---|---|---|
| 14 | $CH_3$ | $CH_3$ | Cl | bond | 3-$CH_3$O— |
| 15 | $CH_3$ | $CH_3$ | Br | bond | 4-$CH_3$O— |
| 16 | $CH_3$ | $CH_3$ | Cl | bond | 4-$C_2H_5$O— |
| 17 | $CH_3$ | $CH_3$ | Br | bond | 4-n-$C_4H_9$— |
| 18 | $CH_3$ | $CH_3$ | Cl | bond | 4-$CH_3$—CH=CH |
| 19 | $CH_3$ | $CH_3$ | Br | bond | 4-$CH_3$—$CH_2$—CH($CH_3$) |
| 20 | $CH_3$ | $CH_3$ | Cl | bond | 4-n-$C_3H_7$ |
| 21 | $CH_3$ | $CH_3$ | Br | bond | 3-$C_2H_5$ |
| 22 | $CH_3$ | $CH_3$ | Cl | bond | 3-$C_2H_5$ |
| 23 | $CH_3$ | $CH_3$ | Cl | bond | 4-sec.-$C_4H_9$ |
| 24 | $CH_3$ | $CH_3$ | Cl | epoxide | 4-$C_2H_5$ |
| 25 | $CH_3$ | $CH_3$ | Cl | epoxide | H |
| 26 | $CH_3$ | $CH_3$ | Br | epoxide | 4-$CH_3$ |
| 27 | $CH_3$ | $CH_3$ | Cl | epoxide | 4-i-$C_3H_7$ |
| 28 | $CH_3$ | $CH_3$ | Cl | epoxide | 4-$NO_2$ |
| 29 | $CH_3$ | $CH_3$ | Br | epoxide | 3-Cl |
| 30 | $CH_3$ | $CH_3$ | Cl | epoxide | 4-Cl |
| 31 | $CH_3$ | $CH_3$ | Cl | epoxide | 4-Br |
| 32 | $CH_3$ | $CH_3$ | Br | epoxide | 4-I |
| 33 | $CH_3$ | $CH_3$ | Cl | epoxide | 4-F |
| 34 | $CH_3$ | $CH_3$ | Cl | epoxide | 4-CN |
| 35 | $CH_3$ | $CH_3$ | Cl | epoxide | 3-$CH_3$O— |
| 36 | $CH_3$ | $CH_3$ | Br | epoxide | 4-$CH_3$O— |
| 37 | $CH_3$ | $CH_3$ | Cl | epoxide | 4-$C_2H_5$O— |
| 38 | $CH_3$ | $CH_3$ | Br | epoxide | 4-n-$C_4H_9$— |
| 39 | $CH_3$ | $CH_3$ | Cl | epoxide | 4-$CH_3$—S— |
| 40 | $CH_3$ | $CH_3$ | Br | epoxide | 4-$CH_3$—CH=CH |
| 41 | $CH_3$ | $CH_3$ | Cl | epoxide | 4-$CH_3$—$CH_2$—CH($CH_3$) |
| 42 | $CH_3$ | $CH_3$ | Br | epoxide | 4-n—$C_3H_7$ |
| 43 | $CH_3$ | $CH_3$ | Cl | epoxide | 4-$C_2H_5$ |
| 44 | $CH_3$ | $CH_3$ | Br | epoxide | 3-$C_2H_5$ |
| 45 | $CH_3$ | $CH_3$ | Cl | epoxide | 4-sec.-$C_4H_9$ |
| 46 | $CH_3$ | $CH_3$ | Cl | H | H |
| 47 | $CH_3$ | $CH_3$ | Cl | H | 4-$CH_3$ |
| 48 | $CH_3$ | $CH_3$ | Br | H | 4-i-$C_3H_7$ |
| 49 | $CH_3$ | $CH_3$ | Cl | H | 4-$NO_2$ |
| 50 | $CH_3$ | $CH_3$ | Cl | H | 3-Cl |
| 51 | $CH_3$ | $CH_3$ | Br | H | 4-Cl |
| 52 | $CH_3$ | $CH_3$ | Cl | H | 4-Br |
| 53 | $CH_3$ | $CH_3$ | Cl | H | 4-I |
| 54 | $CH_3$ | $CH_3$ | Br | H | 4-F |
| 55 | $CH_3$ | $CH_3$ | Cl | H | 4-CN |
| 56 | $CH_3$ | $CH_3$ | Cl | H | 3-$CH_3$O— |
| 57 | $CH_3$ | $CH_3$ | Br | H | 4-$CH_3$O— |
| 58 | $CH_3$ | $CH_3$ | Cl | H | 4-$C_2H_5$O— |
| 59 | $CH_3$ | $CH_3$ | Br | H | 4-n-$C_4H_9$ |
| 60 | $CH_3$ | $CH_3$ | Cl | H | 4-$CH_3$—S— |
| 61 | $CH_3$ | $CH_3$ | Cl | H | 4-$C_2H_5$ |
| 62 | $CH_3$ | $CH_3$ | Br | H | 4-$C_2H_5$ |
| 63 | $CH_3$ | $CH_3$ | Br | H | 4-$CH_3$—CH=CH |
| 64 | $CH_3$ | $CH_3$ | Cl | H | 4-$CH_3$—$CH_2$—CH($CH_3$) |
| 65 | $CH_3$ | $CH_3$ | Br | H | 4-n—$C_3H_7$ |
| 66 | $CH_3$ | $CH_3$ | Cl | H | 3-$C_2H_5$ |
| 67 | $CH_3$ | $CH_3$ | Br | H | 3-$C_2H_5$ |
| 68 | $CH_3$ | $CH_3$ | Cl | H | 4-sec.-$C_4H_9$ |

INSECTICIDAL EVALUATION TEST

The degree of activity of a candidate compound to hinder or impede the metamorphosis of insects is measured by treating the penultimate larval stage of a representative insect with the compound and examining it after its last molt toward the adult form for retention of immature features.

Specifically, yellow mealworm, Tenebrio molitor, L., larvae are maintained at 28°C. and 40% humidity on a diet of bran flakes. Prepupae care collected from the culture and kept in separate containers. The pupae collected once daily, are 1–25 hours old at the time of treatment. By means of a syringe, suitable amounts of candidate compounds in 0.5 or 1.0 μl of acetone are applied to the venter of Tenebrio molitor, L. pupae. Treated pupae are maintained at 28°C. and 40% humidity until the adults emerged (usually within 6–8 days). Emerged adults are graded as positive, negative, or dead. To be considered a positive response, the presence of typical pupal cuticle, urogomphi, gin trap, and abnormal wings, etc., are required. For each test, 2 groups of 20 pupae were used and the averaged results were reported.

The dose of a candidate compound per pupa that is needed to kill or give a positive response in the above insecticidal evaluation test for 10 of the 20 pupae is determined. Table II shows these doses under the column $ED_{50}$.

TABLE II

| COMPOUND NUMBER | $ED_{50}$-μg/pupa |
|---|---|
| 1 | 0.3 |
| 2 | 0.1 |
| 3 | 0.5 |
| 24 | 0.03 |

The compounds of this invention are generally embodied into a form suitable for convenient application. For example, the compounds can be embodied into pesticidal composition which are provided in the form of emulsions, suspensions, solutions, dusts, and aerosol sprays. In general, such compositions will contain, in addition to the active compound, the adjuvants which are found normally in pesticide preparations. In these compositions, the active compounds of this invention can be employed as the sole pesticide component or they can be used in admixture with other compounds having similar utility. The pesticide compositions of this invention can contain, as adjuvants, organic solvents, such as sesame oil, xylene range solvents, heavy petroleum, etc.; water; emulsifying agents; surface active agents; talc; pyrophyllite; diatomite; gypsum; clays, propelants, such as dichlorodifluoromethane, etc. If desired, however, the active compounds can be applied directly to feedstuffs, seeds, etc. upon which the pests feed. When applied in such a manner, it will be advantageous to use a compound which is not volatile. In connection with the activity of the presently disclosed pesticidal compounds, it should be fully understood that it is not necessary that they be active as such. The purposes of this invention will be fully served if the compound is rendered active by external influences, such as light or by some physiological action which occurs when the compound is ingested into the body of the pest.

The precise manner in which the pesticidal compositions of this invention are used in any particular instance will be readily apparent to a person skilled in the art. Generally, the active pesticide compound will be embodied in the form of a liquid composition, for example, an emulsion, suspension, or aerosol spray.

While the concentration of the active pesticide in the present compositions can vary within rather wide limits, ordinarily the pesticide compound will comprise not more than about 15.0% by weight of the composition. Preferably, however, the pesticide compositions of this invention will be in the form of solutions or suspensions containing about 0.1 to 1.0% weight of the active pesticide compound.

What is claimed:

1. A method of controlling *Tenebrio molitor* comprising applying thereto at any stage of their development a metamorphosis hindering amount of a compound of the formula:

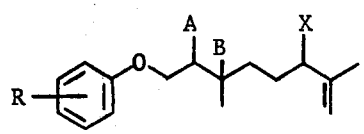

in which R is 4-alkyl having 1 to 4 carbon atoms; or 4-alkylthio having 1 to 4 carbon atoms; X is chlorine or bromine; and A and B together form a bond.

2. The process of claim 1 in which X is chlorine, R is 4-alkyl having 1 to 4 carbon atoms and A and B together form a bond.

3. The process of claim 1 in which X is bromine; R is 4-alkyl having 1 to 4 carbon atoms and A and B together form a bond.

4. The process of claim 1 in which X is chlorine; R is 4-alkylthio having 1 to 2 carbon atoms and A and B together form a bond.

5. The process of claim 4 in which R is 4-methylthio.
6. The process of claim 2 in which R is 4-ethyl.
7. The process of claim 3 in which R is 4-ethyl.

* * * * *